(12) United States Patent
Godin et al.

(10) Patent No.: US 9,107,975 B2
(45) Date of Patent: Aug. 18, 2015

(54) ACIDIC GASES PERMEATED CARBOXYALKYL STARCH AND ALKALINE STARCH EXTRUDATES AND PROCESS FOR MAKING THE SAME

(75) Inventors: Danick Godin, St-Bruno-de-Montarville (CA); George Koutlakis, Verdun (CA); Nicolas Nourry, St-Amble (CA)

(73) Assignee: Archer Daniels Midland Co., Decatur, IL (US)

( * ) Notice: Subject to any disclaimer, the term of this patent is extended or adjusted under 35 U.S.C. 154(b) by 982 days.

(21) Appl. No.: 13/202,456

(22) PCT Filed: Feb. 22, 2010

(86) PCT No.: PCT/US2010/024872
§ 371 (c)(1),
(2), (4) Date: Aug. 19, 2011

(87) PCT Pub. No.: WO2010/096742
PCT Pub. Date: Aug. 26, 2010

(65) Prior Publication Data
US 2011/0297185 A1    Dec. 8, 2011

Related U.S. Application Data

(60) Provisional application No. 61/154,119, filed on Feb. 20, 2009.

(51) Int. Cl.
*A61L 15/42* (2006.01)
*A61L 15/28* (2006.01)
(Continued)

(52) U.S. Cl.
CPC .................. *A61L 15/42* (2013.01); *A61L 15/28* (2013.01); *A61L 15/60* (2013.01); *C08B 31/006* (2013.01);
(Continued)

(58) Field of Classification Search
CPC ....... A61L 15/28; A61L 15/42; C08B 31/006; C08B 31/12; C08J 7/14; C08J 303/08; C08J 3/075; C08J 3/245; C08K 3/24; C08L 3/08
USPC .......... 252/194, 190; 536/102, 104, 106, 107, 536/108, 109, 110, 111; 134/7; 502/404; 514/60
See application file for complete search history.

(56) References Cited

U.S. PATENT DOCUMENTS 3,345,358 A * 10/1967 Inklaar .......................... 536/106
3,391,135 A   7/1968 Ouno et al.
(Continued)

FOREIGN PATENT DOCUMENTS

NL         9100249         2/1991
(Continued)

OTHER PUBLICATIONS

Korean Intellectual Property Office, Written Opinion of the International Searching Authority, International Application No. PCT/US2010/024872, Nov. 11, 2010, pp. 1-4.
(Continued)

*Primary Examiner* — Joseph D Anthony
(74) *Attorney, Agent, or Firm* — Vincent T. Kung; Mark W. Roberts

(57) ABSTRACT

The present disclosure relates to particles comprising carboxyalkyl starch that are permeated with an acidic gas and their uses as absorbent materials. It was discovered that superabsorbent materials could be obtained from carboxyalkyl starch particles permeated with the acidic gas and heated to a temperature of at least 100° C. until they reach an AUL at 0.7 psi. of at least 14 g/g and a CRC of at least 18 g/g. Moreover, it was discovered that the pH of alkaline starch extrudates can be adjusted by permeating particles of the extrudate with the acidic gas even with treating the particles to temperatures less than 100° C. The carboxyalkyl starch particles obtained by the methods described herein are characterized as having intramolecular ester bonds, which are greater in number at the surface of the particle than in the core, and the particles have a greater concentration of cation of the acidic gas at the surface than a the core.

16 Claims, 5 Drawing Sheets

(51) Int. Cl.
    *A61L 15/60*     (2006.01)
    *B08B 7/00*     (2006.01)
    *B01J 20/30*     (2006.01)
    *C09K 17/32*     (2006.01)
    *B01J 20/28*     (2006.01)
    *C08B 31/00*     (2006.01)
    *C08B 31/12*     (2006.01)
    *C08K 3/24*     (2006.01)
    *C08J 3/075*     (2006.01)
    *C08J 3/24*     (2006.01)
    *C08J 7/14*     (2006.01)

(52) U.S. Cl.
    CPC .................. *C08B 31/12* (2013.01); *C08J 3/075* (2013.01); *C08J 3/245* (2013.01); *C08J 7/14* (2013.01); *C08K 3/24* (2013.01); *C08J 2303/08* (2013.01)

(56) References Cited

U.S. PATENT DOCUMENTS

| | | |
|---|---|---|
| 4,044,766 A | 8/1977 | Kaczmarzyk et al. |
| 4,200,737 A | 4/1980 | Marder et al. |
| 4,959,341 A | 9/1990 | Wallach |
| 5,079,354 A | 1/1992 | Gross et al. |
| 5,550,189 A | 8/1996 | Qin et al. |
| 6,769,042 B2 | 7/2004 | Kato et al. |
| 8,461,129 B2 * | 6/2013 | Bolduc et al. .......... 514/54 |
| 8,710,212 B2 * | 4/2014 | Thibodeau et al. ..... 536/47 |
| 2007/0179291 A1 * | 8/2007 | Thibodeau et al. ..... 536/47 |
| 2008/0177057 A1 * | 7/2008 | Bolduc et al. .......... 536/123.1 |
| 2013/0296548 A1 * | 11/2013 | Godin et al. ........... 536/107 |

FOREIGN PATENT DOCUMENTS

| | | |
|---|---|---|
| WO | 0035504 A1 | 6/2000 |
| WO | 2005123781 A2 | 12/2005 |
| WO | 2008037082 A1 | 4/2008 |

OTHER PUBLICATIONS

Korean Intellectual Property Office, International Search Report, International Application No. PCT/US2010/024872, Nov. 12, 2010, pp. 1-4.

\* cited by examiner

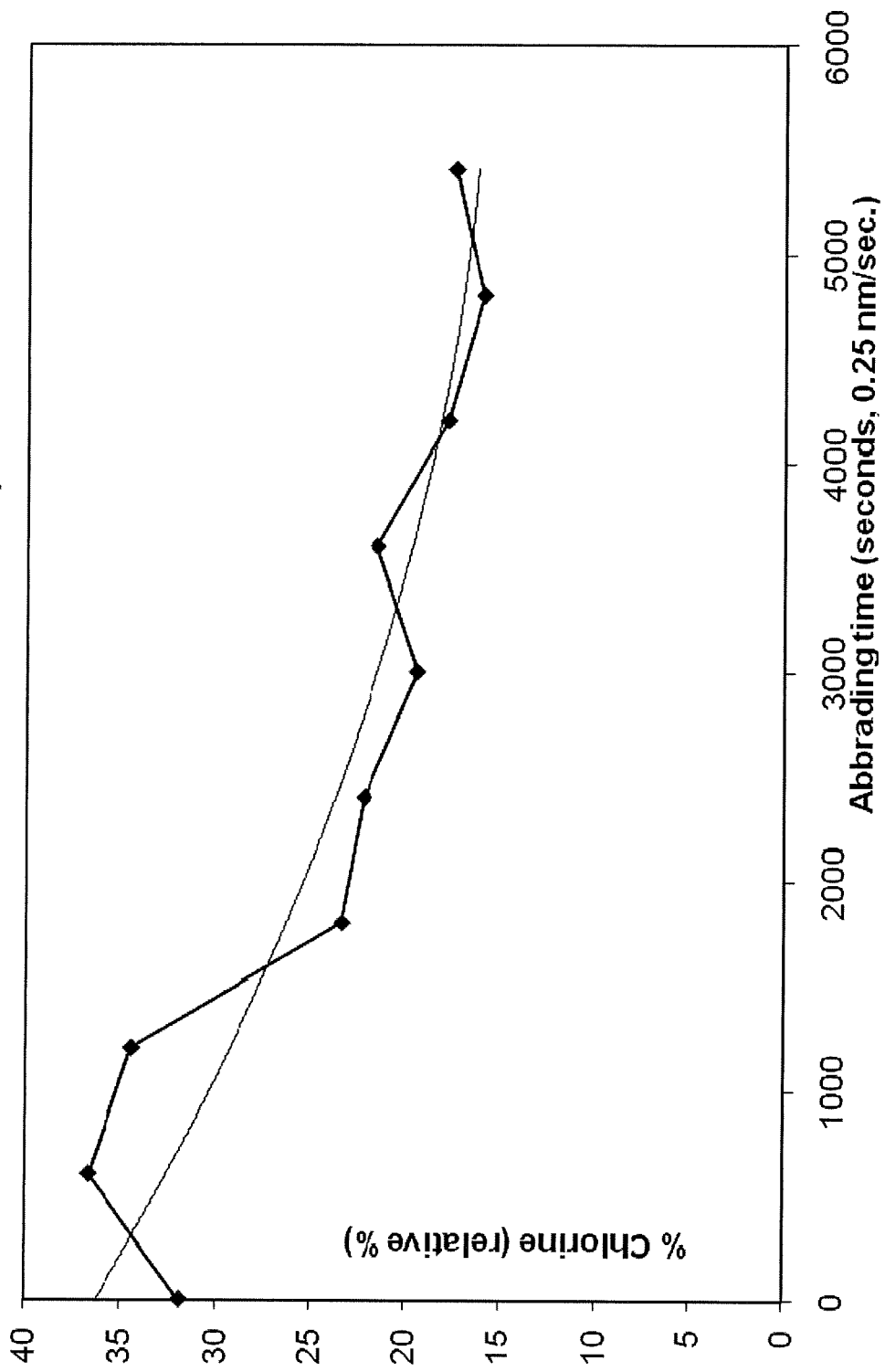

ACIDIC GASES PERMEATED CARBOXYALKYL STARCH AND ALKALINE STARCH EXTRUDATES AND PROCESS FOR MAKING THE SAME

CROSS REFERENCE TO RELATED APPLICATIONS

This application is a national phase entry of PCT/US2010/024872 filed Feb. 22, 2010, which claims priority to U.S. provisional application No. 61/154,119 filed Feb. 20, 2009, each of which are incorporated herein by reference in their entirety.

TECHNICAL FIELD

The present disclosure relates to acidic gas permeated particles comprising carboxyalkyl starch and subsequent treatments thereof for making bio based superabsorbent polymers. In particular, there is disclosed a process for gas permeation and surface treatment of particles comprising carboxyalkyl starches. In a more particular aspect, there is disclosed a process for the neutralization of alkaline starch extrudates by permeating with an acidic gas. Also disclosed are compositions of carboxyalkyl starches and alkaline starch extrudates made thereby, along with their uses and formulations.

BACKGROUND

Water absorbent materials, such as superabsorbent polymers, can be employed in various applications such as in disposable hygiene articles (i.e. diapers, incontinence articles, feminine hygiene products, airlaids and absorbent dressings), household articles, sealing materials, humectants in agricultural products for soil conditioning, in oil-drilling fluids (i.e. lost-circulation material, fracturing fluids), anti-condensation coatings, in agricultural, horticultural and forestry applications for retaining water in the soil and for the release of water to the roots of plants and trees, in the textile industry, in printing applications, in absorbent paper products, in bandages and surgical pads (i.e. wound dressings), in ore treatments, in concrete products, in pet litter, in water treatment, in food pads (i.e. applications related to the transportation of fresh food and food packaging), in detergents, in fire-fighting gels, in sealing materials, in cloud control, as chemical absorbents for the cleanup of acidic and/or basic aqueous spills including water soluble chemical spills, as polymeric gels for the slow and controlled release of cosmetics and pharmaceuticals (also known as drug delivery systems) and finally in the manufacture of artificial snow. However, the primary use of superabsorbent polymers, also referred as "SAPs", is in disposable personal hygiene articles. Such products include, in decreasing order of volume of superabsorbent materials used, diapers, training pants, adult incontinence products and feminine hygiene products.

With the development of ultra-thin products, superabsorbent requirements increased. Not only superabsorbents need to absorb large amounts of liquids, but they need also to retain those liquids under stress, swell under pressure and even have a specific gel particle behavior when swollen, as to permit liquids to flow. Among superabsorbents, polyacrylates are widely used today. But current polyacrylates are not bio-based, leading to increased carbon footprint, depletion of non-renewable oil reserves and increased vulnerability to energy pricing fluctuations. As an alternative, carboxymethyl cellulose (CMC) is partly biobased and has long been for use as a superabsorbent material.

The major problem of CMC, however, lies in its excessive solubility in water, which causes poor performance properties when deployed as a superabsorbent material. Moreover, the manufacture of CMC typically results in material with an unnecessarily high amount of substitution (carboxylation) per residue, i.e., greater than 0.7 substitutions per residue. Because carboxylation requires the use of petroleum based organic reactants, the excessive carboxylation means increased material cost, a lower degree of renewable matter, and increased carbon footprint. Chatterjee et al.; U.S. Pat. No. 3,731,686; Reid et al.; U.S. Pat. No. 3,379,721 and Ning et al; U.S. Pat. No. 5,247,072 each described means to insolubilize CMC by heat treatment. Acidification has also been described as a means for insolubilization of by CMC Reid et al.; U.S. Pat. No. 3,379,720; Thornton et al.; U.S. Pat. No. 6,765,042 and Kaczmarzyk et al.; U.S. Pat. No. 4,044,766. The major problem with these types of acidification is the use of a liquid solvent as the acid carrier requiring costly liquid handling step, additional energy to dry the solvent. In order to solve those problems, acidic gases had been used to treat CMCs particles, such as described in Ouno et al. U.S. Pat. No. 3,391,135 and Marder et al. U.S. Pat. No. 4,200,737. However, CMCs still have several drawbacks which made them unsuitable as absorbents. One major drawback is that highly absorbent CMCs are very specific to certain types of cellulose fibers meaning that the manufacture of a consistent product requires specific sources of cellulose fibre. Moreover, cellulose fibers from almost all natural sources are occur in a crystalline pattern that must be broken by the carboxymethylation reaction itself, resulting in differential and unpredictable substitution patterns through the cellulose polymer.

Carboxymethyl Starch (CMS) absorbents were far less investigated than CMC. Gross U.S. Pat. No. 5,079,354 and Qin et al. U.S. Pat. No. 5,550,189 described CMS absorbents. Due to water-based reaction inefficiencies or, alternatively, poor performances of dry or solvent synthesis, CMS was only reluctantly explored as a bio based absorbent material. Theodorus et al. NL P 9100249A described CMS extrudates as a possible material for use absorbents. However, the process for manufacture described by Theodorus et al. used excesses of monochloroacetates to generate hydrogen chloride in-situ and resulted in material with significant amounts of residual salts inside the CMS particle, and the particles were uniformly acidified throughout rather than being surface treated as described in more detail herein after. Perhaps due to both the lack of surface treatment and the presence of high amounts of salts, the CMS materials described by Theodorus et al. cannot reach acceptable industry specifications for use as superabsorbent materials for diaper applications, such as having an Absorbency Under Load (AUL) at 0.7 psi of at least 14 g/g and a centrifuge retention capacity (CRC) of at least 18 g/g. More recently, Koutlakis al. US App. 2008/177057A1 described a solvent based treatment of CMS extrudates that resulted in CMS particles with an AULs of at least 14 g/g. However, because those surface treatments were performed in solvent based systems, those processes have similar problems to those described by; Thornton et al.; such as additional liquid handling steps, additional energy costs and particle attrition, which was referred to in that application as "static environment".

The present disclosure addresses these problems and others, and provides further advantages that one of ordinary skill in the art will readily discern upon understanding the disclosure that follows.

SUMMARY OF THE INVENTION

The present disclosure refers to a number of documents, the content of which are herein incorporated by reference only to the extent needed to provide information and/or a source for materials and methods of making to enable the production of CMS particles by the processes described herein, or to understand terms of art used in the present disclosure, unless the incorporated references includes information that conflicts with the present disclosure, in which case the present disclosure controls and the information incorporated by reference shall be deemed void of the conflicting content.

It was unexpectedly discovered that superabsorbent polymers could be obtained from particles comprising carboxyalkyl starches that have been permeated with an acidic gas followed by a heat treatment. Those absorbent materials could be done by a process comprising the steps of: permeating a particle comprising carboxyalkyl starch with an acidic gas; and. treating the particle to a temperature of at least 100° C. Optionally, the heating step is performed until the carboxyalkyl starch develops an AUL at 0.7 Psi of at least 14 g/g and a CRC of at least 18 g/g.

Moreover, it was discovered that it was possible to adjust pH, even neutralize alkaline starch extrudates particles with an acidic gas. This is also accomplished by permeating an alkaline starch extrudate particle with an acidic gas. Typically, the alkaline starch extrudates are in the form of particles having a size ranging from 150 μm to 850 μm that most typically comprise carboxyalkyl starch, and in more typical embodiments comprises carboxy methyl starch.

In a further embodiment, the present disclosure relates to the use of superabsorbents made from acidic gas permeated particles comprising carboxyalkyl starch. Those particles may be used as absorbents in disposable sanitary products (i.e. diapers, incontinence articles, feminine hygiene products, airlaids and absorbent dressings), household articles, sealing materials, humectants in agricultural products for soil conditioning, in oil-drilling fluids (i.e. lost-circulation material, fracturing fluids), anti-condensation coatings, in agricultural, horticultural and forestry applications for retaining water in the soil and for the release of water to the roots of plants and trees, in the textile industry, in printing applications, in absorbent paper products, in bandages and surgical pads (i.e. wound dressings), in ore treatments, in concrete products, in pet litter, in water treatment, in cloud control, in food pads (i.e. applications related to the transportation of fresh food and food packaging), in detergents, in fire-fighting gels, in sealing materials, as chemical absorbents for the cleanup of acidic and/or basic aqueous spills including water soluble chemical spills, as polymeric gels for the slow and controlled release of cosmetics and pharmaceuticals (also known as drug delivery systems), as airlaids, and finally in the manufacture of artificial snow. Those carboxyalkyl starches could also be used as absorbents for liquids, non-limiting examples of which include water, aqueous solutions, physiological fluids and saline solutions.

In yet a further embodiment, the present disclosure relates to compositions including acidic gas permeated particles comprising carboxyalkyl starch combined with another material. Those compositions typically comprise the carboxyalkyl starch particles and a co-absorbent material. Again, the most typical embodiments comprise carboxy methyl starch particles that have been treated with the acidic gas.

BRIEF DESCRIPTION OF THE DRAWINGS

Having thus generally described the invention, reference will now be made to the accompanying drawings, showing by way of illustration a preferred embodiment thereof, and wherein:

FIG. 5 is a graph illustrating a relative concentration of chlorine by depth of a particle comprising carboxymethyl starch treated with HCL gas according to an embodiment of the present invention. This was done by X Ray Photoelectron Spectroscopy (XPS) with Argon etching.

DETAILED DESCRIPTION OF ILLUSTRATIVE EMBODIMENTS

Definitions

Figure 1:
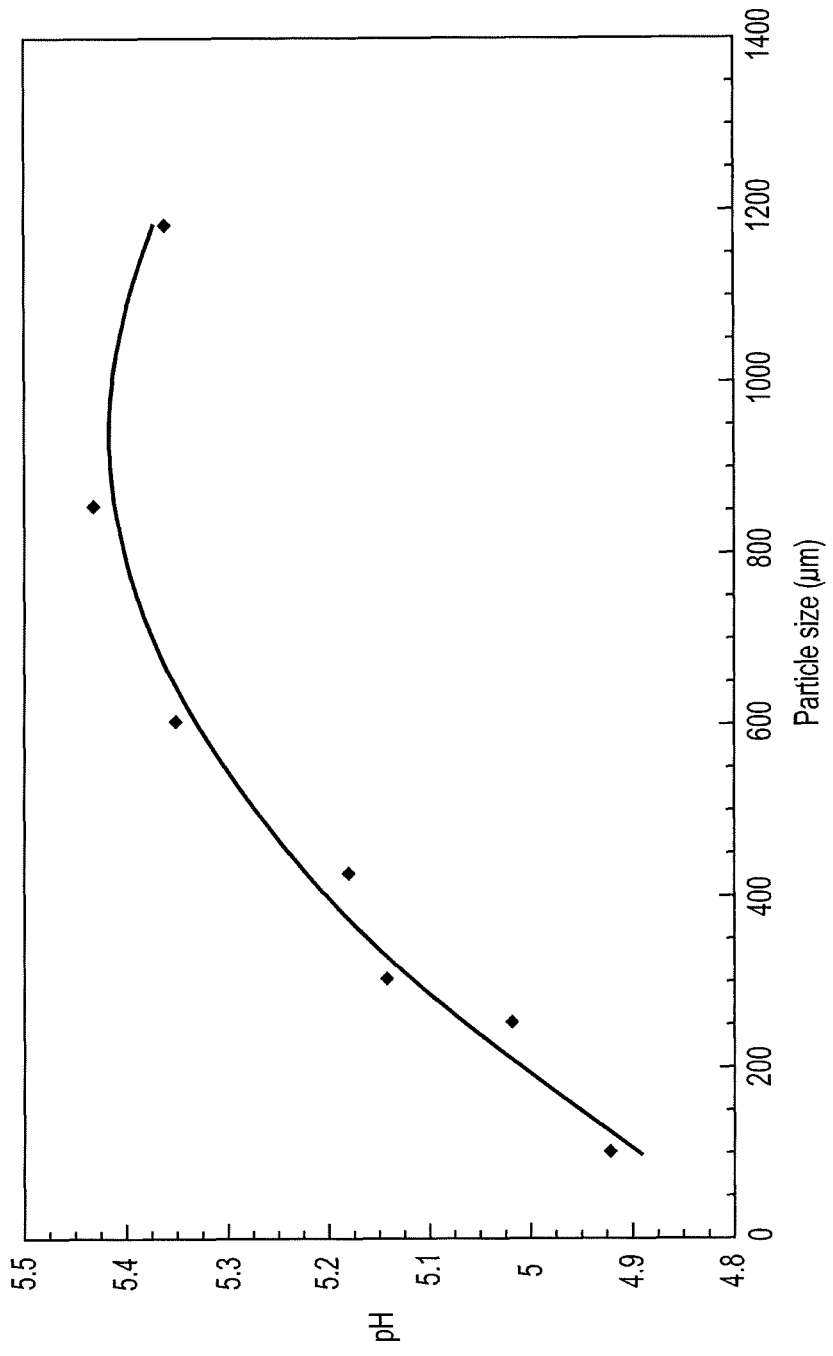
FIG. 1 is a pH particle versus particle size distribution graph of acidic gas permeated carboxyalkyl starch particles according to an embodiment of the present invention.

In order to provide a clear and consistent understanding of the terms used in the present specification, a number of definitions are provided below. Moreover, unless defined otherwise, all technical and scientific terms as used herein have the same meaning as commonly understood by one of ordinary skill in the art to which the present disclosure pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this specification and claim(s), the term "about" with respect to a value means within the degree of error of an instrument that commonly would be used by one of ordinary skill in the art to measure the value in the context of this disclosure, and more particularly, within a range of the stated value where no discernable function or property would differ from the function or property exhibited precisely at the stated value. In non limiting embodiments for various parameters, the term may be within 10%, within 5%, within 1%, and in some cases within 0.5% of the stated value . . . .

As used in this specification, the term "percent" or "%" with respect to a material refers to a percentage by weight (i.e. % (w/w)), unless otherwise specified.

As used in this specification, the term "saline solution" refers to a 0.9% (w/w) sodium chloride solution in deionized water.

As used in this specification, the term "discrete particle" refers to individual particles.

As used in this specification, the term "starch" refers to starch polymers, its components and its derivatives, such as starches, modified starches, amylopectin, modified amylopectin, amylose and modified amylose.

As used in this specification, the term "Free Swell Capacity" (FSC), also called "Total Absorption", refers to the amount (g) of fluid absorbed per gram of the composition. Typical fluids are saline solutions (0.9% Weight/Weight NaCl solution, hereinafter called 0.9% NaCl solution or saline).

As used in this specification, the term "Centrifuge Retention Capacity" (CRC) also called "Retention" refers to the amount (g) of fluid retained per gram of the composition, following exposure of the composition to a centrifugation force of 250G. Typical fluids are saline solutions.

As used in this specification, the term "Absorption Under Load" (AUL), at 0.7 PSI (5 kPa), also called "Absorption Against Pressure" (AAP) or "Absorption Under Pressure" (AUP) refers to the amount (g) of fluid absorbed per gram of the composition under a given applied pressure. Typical fluids are saline solutions (0.9% Weight/Weight NaCl solution, hereinafter called 0.9% NaCl solution or saline).

As used in this specification, the term "absorbent material" or "absorbent polymer" refers to materials in a dry, solid state, having good fluid-swelling properties and capable of gel forming upon contacting with a fluid. Non limiting examples of such fluids are water, aqueous solutions, saline, or physiological fluids.

As used in this specification, the term "superabsorbent", "superabsorbent polymer" or "SAP" refers to absorbent materials capable of gel forming upon contacting with a liquid such as water, aqueous solutions, saline, or physiological fluids. Such materials are characterized by a Centrifuge Retention Capacity (CRC) of at least 15 g/g.

As used in this specification, the term "moisture content" refers to the amount of water (% w/w) contained in a solid.

As used in this specification, the term "granular material", "granules", "particles", "powders", "grains" or "dusts" refers to particulate matter in a finely divided state.

As used in this specification, the term "particle size" refers to the largest dimension of a particle. The particle size can be directly determined using sieving methods, optical or scanning electron microscopes as well as by other well-known methods. Particle size is equivalent in meaning to the diameter of the particle if the particle were perfectly spherical or the length of the particle if oblong.

As used in this specification, the term "discrete gel particles" refers to superabsorbent particles which, once swollen to their maximum extent in saline solution, have an appearance of discrete hydrogel particles.

As used in this specification, the term "particle surface" or "surface zone" refers to the solid outermost layer of a particle. This corresponds to a layer extending from particle's surface to a depth of about one third the particle size.

As used in this specification, the term "particle core" refers to the solid innermost core of a particle. This core is located around the remotest point from the particle surface and extends to the inner most boundary of the particle surface as defined above.

As used in this specification, the term "acidic gas" refers to a material in a gaseous phase that acts as an acid when in contact with humidity or moisture. The acid definition means a Brønsted-Lowry acid, which is a compound able to donate a $H^+$ under the conditions where the acid function is stated.

As used in this specification, "particle pH" or "carboxyalkyl starch pH" or "CMS pH" refers to the pH determined in an equilibrated 10% suspension of the particle in deionized water.

As used in this specification, "particle conductivity" or carboxyalkyl starch conductivity" or "CMS conductivity" refers to the conductivity determined in a 1% suspension of the particle in deionized water.

As used in this specification, "CMS" refers to carboxymethyl starch.

As used in this specification, an "extrudate" is a material formed by an extrusion process whereby an input stream of material in the form of a solid, a gel, an emulsion, suspension, or solution is submitted to pressure and optionally to shear forces such as may be provided by an impeller or screw, so the material is pressed in a chamber against a dye having an orifice that permits the pressed material to emerge from the chamber in the form of a solid, a gel, an emulsion, or particle.

As used in this specification, "permeate" and grammatical variations thereof, means to contact a material with a gas so that the gas spreads over and through at least a portion of the material.

Carboxyalkyl Starch Particles

Among carboxyalkyl starches, carboxymethyl starch is usually contemplated. Carboxymethyl starch provides sufficient osmotic force, but also enough coulombic repulsion forces to achieve high absorbencies under load. In all cases described in this application, carboxymethyl starch should be considered as a typical carboxyalkyl starch.

Carboxyalkylation

Carboxyalkyl functionality may be easily grafted, via ether linkages, to alkalinized starches under a Williamson ether synthesis. This could be easily done with reagents such as leaving groups bearing haloacids and salts thereof. Non-limiting examples of such haloacids are $C_2$-$C_5$ haloacids, such as monochloroacetic acid. Non-limiting examples of salts thereof are alkali metals salts of haloacetic acids, such as sodium monochloroacetate, potassium monochloroacetate, lithium monochloroacetate and mixture thereof. A typical carboxyalkylation reaction could be summarized as follow.

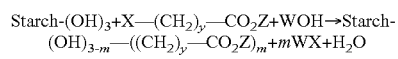

$$\text{Starch-(OH)}_3 + X-(CH_2)_y-CO_2Z + WOH \rightarrow \text{Starch-}(OH)_{3-m}-((CH_2)_y-CO_2Z)_m + mWX + H_2O$$

Wherein Y being the number of alkylene units. X being a nucleophilic leaving group, non-limiting examples of which are chlorine, bromine and iodine. W being an alkali metal. Z being an hydrogen, alkali metal or ammonium group. m being the degree of substitution of the carboxyalkyl starch.

As contemplated by the present teachings, starch may be characterized as glucose polymer in alpha glycoside linkages with a molecular weight of at least 500,000 g/mol. Starch could come from many sources. Non-limiting examples of starch sources are corn, wheat, potato, yam, cassava, rice, millet, sorghum, barley, oats, beans, favas, peas, lentils, buckwheat, bananas, arracacha, oca, sago, taro, sweet potatoes, waxy species thereof (such as waxy corn) and mixture thereof. Among starch sources, waxy corn, potato, corn and wheat are especially contemplated.

Among the methods for making carboxyalkylated starches, starches carboxyalkylated after having been dispersed in an alkaline aqueous medium are believed to be the most suitable choice. Without being bound to any theory, it is believed that carboxyalkylating agents, catalysts and starch chains are more labile in aqueous environment. Starch structure is more easily penetrated by hydroxides and carboxyalkylating agents, as starch is gelatinized and its semi-crystalline pattern is loosened. This gives the resulting effect that carboxyalkyl groups are more evenly substituted and gives increased absorbent characteristics. A non-limiting example of aqueous alkaline medium is an aqueous environment characterized by a pH of at least 11.0. Such pH could be achieved by dispersing an alkali hydroxide in water. Non-limiting examples of such hydroxides are sodium hydroxide, lithium hydroxide and potassium hydroxide. Typical moisture content in such aqueous alkaline medium may range from 15% to 99%.

In a contemplated form of the present invention, the starch is carboxyalkylated by a reactive extrusion process. This allows substantial increases in reaction efficiency and decreases reaction time. Starch is an ideal substance for extrusion. In order to gelatinize, starch requires a sufficient amount of water plus alkali and/or heat. In reactive extrusion, the starch, water and alkali are added in controlled amounts and after mixing, heat is applied to the reactive chamber of the extruder, allowing the starch to be carboxylated and to gel only when needed, more specifically, near the extruder's kneading elements. This process not only limits unwanted side reactions, but also limits molecular weight degradation and reduces energy requirements. The total water content in the carboxyalkylation-extrusion reactions typically ranges from 15% to 30%. This decreased amount of water, compared to solution based carboxyalkylation, provides higher reaction efficiency.

Typically, carboxyalkylation by reactive extrusion is performed using a twin screw extruder. Twin screw extruders provide the flexibility and the shear necessary to perform carboxyalkylation with high efficiency at relatively low moisture content. First, dry ingredients, such as starch and the carboxyalkylating agent are fed into the extruder. The dry ingredients are conveyed to an alkali (hydroxide) injection point, which is located nearer the kneading elements. The alkali is typically injected as a hydroxide solution. Water may be optionally injected. Moisture typically reaches a content ranging from 15% to 30% of the reaction components in the extruder. In order to limit reagent degradation in the extruder, temperature is conveniently kept at no greater than 140° C. Under r these conditions, an alkaline aqueous dough comprising carboxylated and gelatinized starch is produced. The dough is optionally pumped into a die to obtain extrudate strands or pellets. Those extrudates are usually dried by convection means in a fluid bed drier to a moisture content ranging between 5% and 15%, which is needed to subsequently grind the extruded material into particles. Particle sizes ranging from 150 μm to 850 μm (20-100 Mesh) are desired for typical superabsorbent applications.

pH Adjustment

Typically, after grinding into particles, the alkaline carboxylated starch extrudate is then permeated with an acidic gas. Particles may be placed in a closed vessel where a partial vacuum could be produced to degas the particles prior to acidic gas permeation. Typically a vacuum of 30 kPa or lower is sufficient. After degassing, the acidic gas is added to permeate the particles. Among acidic gases, gases of mineral acids are preferred. Halogen halides, and more specifically, hydrogen chloride are most typically used. Hydrogen chloride is a strong acid and has a relatively low molecular weight (36.5 g/mol), allowing better permeation through the starch extrudate. Gas permeation may be done in one step or in multiple steps to ensure more thorough permeation of the material. In a multiple step permeation process, between each exposure to the acidic gas for a time sufficient to permeate the particles, the particles are degassed in a partial vacuum to remove bubbles an prevent formation of vapor blocking barriers that would interfere with thorough permeation. A moderate agitation may be done during the permeation process and/or the degassing steps. The temperature is usually kept under 100° C., typically at room temperature (10° C. to 40° C.).

It was found that the pH of alkaline starch extrudates is advantageously adjusted by exposure to the acidic gas during permeation. This pH adjustment step has many advantages. The first advantage is to avoid, or reduce the need to adjust the pH during subsequent processing steps, such as solvent cleaning steps. Another advantage is the increased penetration of acid inside the alkaline starch extrudate particles, as the relatively "dry chemistry" of the gaseous state Moreover salts are more easily extracted from starch extrudate particles having a pH ranging from 5.0 to 8.0. As mentioned herein before, typical starch extrudates are carboxyalkyl starch extrudates, especially carboxymethyl starch extrudates, which tend to form stronger salt bonds between the carboxylate moieties and the cation of the salt at higher pHs.

It was found that grinding the alkaline starch extrudates into particles will help both the neutralization and acidic gas permeation into the alkaline starch extrudates. In order to be ground, the starch extrudates need to have a moisture content of at most 12%. Moisture can be adjusted by drying. Once ground into particles, starch extrudates have a size ranging from 150 μm to 850 μm. Particle size adjustment can be done by grinding mills and sizes selected by sieving. Many types o grinding equipment can be used. Examples of suitable grinding mills are hammer mills or roller mills.

Purification

Carboxyalkyl starch purity is an important consideration. Any significant amounts of residual impurities may lead to "salt poisoning", which will cause performances reduction. To remove those salts, it is therefore typical to perform a purification step. The carboxyalkyl starch can be at least partially purified of salts by washing with water and a water soluble organic solvent. Non-limiting examples of water soluble organic solvents include $C_1$-$C_4$ alcohols and $C_1$-$C_4$ alcohol/water mixtures. Among $C_1$-$C_4$ alcohols, methanol, and more specifically, methanol/water mixtures are contemplated. Is it useful to keep the water content of such mixtures under the agglomeration threshold. Agglomeration threshold will cause carboxyalkyl starch particles to agglomerate and form masses during the cleaning step. Keeping under agglomeration threshold can be done by carefully selecting the water concentration in the solvent and controlling the temperature of the washing step. Non-limiting examples are a 85/15 (v/v) methanol/water mixture at 60° C. or, a 75/25 (v/v) mixture at 22° C. Once the solvent has been used to clean the washed material, the carboxyalkyl starch particles s are filtered and dried. The use of a "dryer" solvent, at the end of the solvent washing may ease drying, as it will remove water and prevent lump formation during subsequent steps. The dryer solvent may also be a water miscible organic solvent with less water content than the washing solvent, for example at least 90% methanol or ethanol. Carboxyalkyl starches may be considered purified when they comprise less than 1% sodium chloride or characterized as sufficiently cleaned of salt when a 1% suspension of the particles in deionized water has a conductivity of at most 1,500 μS/cm. The washing solvent and the dryer solvent may be recycled and reused by purification over an ion exchange resin to remove the extracted salts.

After the washing step, is it usual to adjust the carboxyalkyl starch particles moisture content and bulk density. Carboxyalkyl starch particles are typically filtered from washing and drying solvents of the cleaning step. Upon drying, organic miscible solvents will usually evaporate before water. This will cause a relative moisture increase in the carboxyalkyl starch particles, which will change the density of the carboxyalkyl starch particle to a range from 0.5 to 0.7 g/cm³. The moisture is also decreased to a content advantageously not greater than 12%. It is possible that agglomerates could form during the drying step depending on the drying technique. The larger agglomerate s can be recovered after sieving and reground by grinding means, such as hammer or roller mills. The desired particle size, after the entire process is typically still from 150 µm to 850 µm (100 Mesh to 20 Mesh).

Permeation/Heating

Applicants surprisingly discovered that permeation of carboxyalkyl starch particles with gaseous acid, followed by a heat treatment at a temperature of at least 100° C. insolubilizes the otherwise soluble carboxyalkyl starch fraction of the particles. Even more interesting, applicants discovered that by a combination of proper heating time and temperature, it was possible to cure the acidic gas treated particles in so that they reached an AUL at 0.7 Psi of at least 14 g/g, without decreasing CRC below 18 g/g or FSC below 28 g/g.

Particles comprising carboxyalkyl starch to be permeated usually have many characteristics, inferred from steps such as those described previously. Particles comprising carboxyalkyl starch typically have a bulk density usually ranging from 0.5 g/cm³ to 0.7 g/cm³. Typically, carboxyalkyl starches have a degree of carboxyalkyl substitution (as determined by ASTM D1439-83a method) ranging from 0.3 to 1.0 per residue. Those having a degree of substitution ranging from 0.4 to 0.7 are even more usual. Particles, when permeated, washed and dried according to the present teaching should have a moisture content of not greater than 12%. A particle moisture content ranging between 0% and 8% is most suitable. Moisture content selection will adversely impact atmospheric pressure during the heat treatment step as will be described herein later. Suitable carboxyalkyl starch particles made according to the present teaching are characterized also by having pH ranging from 5.5 to 7.5 when measured in a 10% (w/w) suspension with deionized water more usually having a pH ranging from 6.2 to 6.8. They are relatively pure, typically containing less than 1% sodium chloride and are characterized by having conductivity of less than 1500 µS/cm as measured in a 1% suspension with deionized water.

Carboxyalkyl starch particles comprising an even distribution of carboxyalkyl groups have promising structural characteristics. Indeed, because alkaline dispersion during synthesis provides for the carboxyalkyl groups to be evenly substituted throughout the starch, carboxyalkyl groups are also found evenly distributed throughout the starch particle core and particle surface. As acidic gas permeates the particle catalyzing formation of esters with the carboxyl groups, there is obtained an even distribution of esters in a gradient that has fewer esters in the particle core than on the surface, making the surface more rigid and the core more porous thereby producing particles with higher CRCs.

It was surprising and advantageously discovered that permeation of carboxyalkyl starch particles with acidic gas in is not even throughout the particle. As mentioned herein above, the particles are typically selected to have a size from 150 µm to 850 µm. It was discovered that after the gaseous acid treatment, particles having a size ranging from 150 µm to 250 µm have a lower pH (in a 10% w/w suspension in water) than particles having a size ranging from 600 µm to 850 µm. Particles having a size ranging from 150-250 µm typically have a pH ranging from 4.80 to 5.00 in that suspension while particles having a size ranging from 600 µm to 850 µm typically have a pH ranging from 5.35 to 5.50. It is believed that a particle's core can be more easily penetrated by the acid permeation process when the particles are smaller (e.g. thickness effect), and therefore the measured pH in the suspension of smaller particles is significantly lower than that for the larger particles. This phenomenon is best depicted in FIG. 1, which illustrates a correlative relationship between particle size and pH, with a sharply lower pH being associated with smaller particles. Additionally, this phenomenon was further characterized by X-Ray photoelectron spectroscopy, as depicted in Figure, which shows that the relative concentration of acidic gas anions (in this case chlorine) at the surface of the particles is higher than the concentration in the interior of the particle (the core) at a depth exposed after 5400 seconds of Argon abrading time. In this case, the relative concentration of chlorine at 5400 seconds of Argon abrading time is at least 10% lower than the relative concentration at zero seconds of abrading time. In-fact, FIG. 5 shows that the relative chlorine relative concentration is relatively constant and 30% higher in the material exposed within the first 1500 seconds of Argon abrading time in comparison to the material exposed at 5400 seconds and there is a regular correlation between particle depth and chlorine concentration between these times.

As mentioned herein above, permeation may be conducted in multiple steps with degassing in between. The information presented herein regarding pH and chlorine concentration provides a method for measuring effective permeation. Between each permeation step the pH may be assessed in a 10% (w/w) water suspension. Determination of pH values ranges from 4.5 to 5.5, and more desirably from 5.3 to 5.5 indicates the permeation has been successful and can be stopped when the pH reach those values.

Carboxyalkyl starch particles are allowed to react with the acidic gas and then degassed in a partial vacuum of 30 kPa or less, or more typically 20 kPa or less for the heat treatment step. A partial vacuum of 3 kPa is typical, as it allows a wider flexibility in both temperature rise rate and initial moisture content. Pressure of 20 kPa will require more minute adjustments of temperature rise rate as well as higher initial moisture content. A moderate agitation can be done during the permeation time, the reacting time, degassing time or the heat treatment time. Once degassed after permeation, and once the carboxyalkyl starch has reached the target pH, the temperature is raised to above 100° C. The hotter the carboxyalkyl starch particles are the lesser the time they need to be heat exposed to obtain suitable performance properties. Heating is typically performed between 115° C. and 140° C. Heating time and temperature are sufficient when the carboxyalkyl starch particles reach an AUL at 0.7 psi of at least 14 g/g and before their CRC decreases to under 18 g/g which will occur with prolonged heating or heating at too great of a temperature. The particles should also be optionally characterized by having a FSC of at least 28 g/g.

Heating can be performed b direct conductive contact with the particles with a heated gas by convection or by radiant contact. Typically, heating is performed in the same closed vessel used for permeation. The heating source may be for example, an electromagnetic radiation source, a hot gas, a radiant heat element or a heated surface. Typically, infrared radiation sources identified as medium infra-red or carbon infra-red are also well suited.

In addition of absorbent performance characteristics, the carboxyalkyl starch particles will form an insoluble gel when swollen. This insoluble gel will be made from a compendium of discrete gel particles. Because the gel particles are discreet and non agglomerated, aqueous solutions are able to flow between and through the discreet gel particles allowing for even distribution of the fluid throughout the compendium of particles. This is an especially desired feature of diapers, as liquid penetration occurs through all axes of an absorbent core.

Without being bound to any theory, it is believed that the acidic gas acts as catalyst that accelerates a Fischer-esterification between starch hydroxyl groups and the carboxylate groups of the carboxyalkyl moieties leading to intramolecular esterification between these functional groups, particularly at the particle's surface. While the intramolecular esterification must cross link different portions of the starch polymer, this is not the same surface cross linking as using a cross linking agent, because in the present teaching, no cross linking agent is used, rather the HCL acid is merely acting as a catalyst to cause intramolecular esterification to occur. Surprisingly, these intramolecular esters do not decrease centrifuge retention capacity to under 18 g/g. The degree of intramolecular-esterification may be controlled by various means, for example, by controlling the amount of acidic gas used during permeation, controlling the pressure of acidic gas permeation process, varying the moisture content of the particle or acidic gas, varying the pressure during the heating treatment process, as well as controlling the temperature rise during the heat treatment. Because intramolecular esterification is catalyzed by the acid, and it has been demonstrated that the acid does not uniformly penetrate the particle, but rather penetrates the particle more at the surface than the core, it follows that the particles produced by acidic gas permeation will also have fewer intramolecular esters formed in the interior core than at the surface. Dissection of a sample of particles and measurement of the esters formed in various sections would demonstrate a similar gradient of ester formation as the gradient of chlorine distribution found and depicted in FIG. 5.

Ester formation can be determined by a variety of techniques. One technique is to chemically measure ester bonds by dissolving 0.05 of the particles in 1 ml of a solution of hydroxylammonium chloride. Then 4 drops of 20% (w/w) NaOH solution are added and the mixture is brought to 72° C. for 2 minutes and allowed to cool to room temperature (22° C.). Then, 2 ml of 1N solution of HCl is added. If the solution becomes milky, 2 ml of ethanol (95% w/w) is added. Then dropwise, a solution of ferrous chloride (5 g of $FeCl_3$ in 100 ml of deionized water) is added. Ester linkages are detected when the solution becomes purple and degree of ester formation can be determined by spectrophotometric measurement of the evolved color.

The particles of the present disclosure may be mixed with other co-absorbent materials to provide absorbent compositions. In an exemplary embodiment, the absorbent compositions may comprise from about 1 to about 99% (w/w) of carboxyalkyl starch, and from about 99 to about 1% (w/w) of co-absorbent material. Non-limiting examples of co-absorbent materials include synthetic absorbent polymers, starch-based absorbents, mannose containing polysaccharides, fibers and mixtures thereof.

Non-limiting examples of starch-based absorbents include glass-like starches such as disclosed by Huppé et al. (CA 2,308,537); amylopectin networks such as disclosed by Thibodeau et al. (CA 2,462,053); polysaccharide agglomerates such as disclosed by Chevigny et al. (CA 2,534,026); hydroxyethyl starch; hydroxypropyl starch; starch nanocomposites such as disclosed by Berrada et al. (CA 2,483,049); and mixtures thereof.

Non-limiting examples of mannose containing polysaccharides include guar gum, tara gum, locust bean gum, konjac, mesquite gum, psyllium extracts, fenugreek extracts and mixture thereof. The mannose containing polysaccharides may be chemically or enzymatically modified (i.e. mannose derivatives), cross-linked or in the form of nanocomposite materials.

Non-limiting examples of fibers include cellulose, viscose, rayon, cellulose acetate, polyamides (i.e. Nylon™), poly-alkylenes, polyethylene, polypropylene, bi-component fibers, polyesters, polylactides, polypropanediols, polyhydroxyalkanoates, Lyocell™, sphagnum and mixtures thereof.

The synthetic absorbent polymers to be used as co-absorbent materials in the absorbent compositions of the present disclosure, are generally obtained from the polymerization, typically by radical or radical graft polymerization, of monomers, non-limiting examples of which include acrylic acid, acrylate salts, acrylic ester, acrylic anhydride, methacrylic acid, methacrylate salts, methacrylic esters, methacrylic anhydride, maleic anhydride, maleic salts, maleate esters, acrylamide, acrylonitrile, vinyl alcohol, vinyl pyrrolidone, vinyl acetate, vinyl guanidine, aspartic acid, aspartic salts and mixtures thereof.

The particles of the present disclosure, or absorbent compositions comprising such particles, are suitable for use in methods for absorbing liquids. In an embodiment of the present disclosure, one or more of the carboxyalkyl starch particles of the present disclosure are contacted with a liquid to be absorbed. Non-limiting examples of liquids include water, aqueous solutions, physiological fluids and saline solutions. The particles of the present disclosure, upon contacting with the liquid(s) to be absorbed, will form a gel trapping the liquid(s) within.

The particles of the present disclosure could be used in hygiene articles, such as diapers, incontinence products, food pads and sanitary napkins. The particles of the present disclosure may also be used in other applications such as in food pads, in agricultural, horticultural and forestry applications for retaining water in the soil and for the release of water to the roots of plants and trees; in the textile industry, in printing applications, in absorbent paper products, in ore treatments, in concrete additives, in pet litter, in water treatment, in cloud control, in drilling fluids (i.e. lost circulation materials, fracturing fluids); in food pads (i.e. applications related to the transportation of fresh food and food packaging), in detergents, anti-condensation coatings, in fire-fighting gels; in sealing materials, in bandages and surgical pads (i.e. wound dressings); as chemical absorbents for the cleanup of acidic and/or basic aqueous spills including water soluble chemical spills, as polymeric gels for the slow and controlled release of cosmetics and pharmaceuticals (also known as drug delivery systems), and finally in the manufacture of artificial snow. Particles could also be used as absorbents for liquids, non-limiting examples of which include water, aqueous solutions, physiological fluids and saline solutions.

Provided below are experimental protocols and examples to facilitate an understanding of the present disclosure and enable the production of the acidic gas permeated carboxyalkyl particles disclosed herein. These protocols and examples are not by limitation, and are presented as exemplary only. Conditions and details may be modified, added to, or deleted from these examples as selected by the skill of the one of ordinary skill in the art without departing from the essential teaching provided herein.

Materials and Methods

Chemicals: Grade A wheat starch (Whetstar™ 4) was obtained from Archer Daniels Midland (Decatur, Ill.). Sodium monochloroacetate granules were obtained from Akzo-Nobel (Amersfoort, Netherlands). Sulfuric acid was obtained from Fisher (Pittsburgh, Pa.). Sodium hydroxide, sodium chloride, hydrochloric acid and methanol were obtained from Labmat (Quebec City, Canada). Hydrogen chloride was obtained from Air Liquide (Paris, France).

Equipment

Dextrinizer: A NOREDUX COOKER Type F/11 equipped with an internal heated mixing shaft was used. Fluid bed dryer: A Carrier vibrating equipment model QAD/C-1260 S was used to dry carboxymethyl starch extrudates pellets. Pelletizer: A Conair strand cutter was used to cut extrudates strands into pellets (about 1 mm thick, 3 mm diameter). Grinder: A Pallmann grinder type percussion PP8S was used. Convection oven: A Lab tray drier TY 2, National Drying Machinery Company, (Philadelphia, USA) was used. Reactor: A 7000 liters double jacketed stainless steel batch reactor equipped with a shaft with 68 cm long propellers, spaced from 30 cm from the reactor bottom, was used. Infra-red oven: A Panasonic NB-G100P infra-red oven was used. Lab grinder: A Braun™ model KSM grinder was used to grind the samples when in small quantities.

Reactive Extruder

Figure 2:
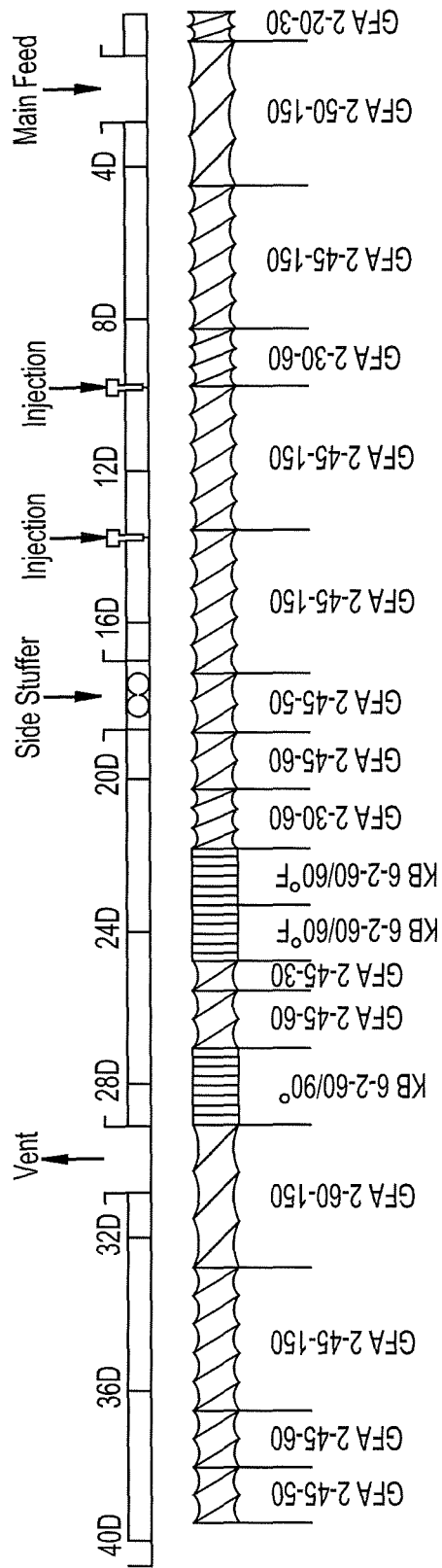
FIG. 2 illustrates a side elevation view of an extruder screw configuration used to manufacture carboxymethyl starches that are treated according to an embodiment of the present invention.

A Leistritz ZSE 40 HP (40 mm) twin screw extruder was used to for reactive carboxyalkylation. The extruder L/D ratio was of 40. Starch was fed with an Acrison gravimetric agitated feeder (405-170-OE). Sodium monochloroacetate was fed with an Acrison gravimetric feeder (405-1015-C). Starch and sodium monochloroacetate were fed between 30 mm and 180 mm. A sodium hydroxide injection nozzle was positioned at 560 mm from the beginning of the extruder, equipped with a Cole-Parmer peristaltic pump. A water injection nozzle was positioned at 720 mm from the beginning of the extruder, equipped also with a Cole-Parmer peristaltic pump. Closed side stuffer barrels were positioned between 640 mm and 800 mm from the beginning. A vent was positioned between 1120 mm and 1280 mm. The screw design is illustrated in FIG. 2 and detailed below.

| Pitch length (mm) | Element length (mm) | Kneading block angle |
|---|---|---|
| Extruder's beginning | | |
| 20 mm | 30 mm | |
| 60 mm | 150 mm | |
| 30 mm | 60 mm | |
| 45 mm | 150 mm | |
| 45 mm | 150 mm | |
| 45 mm | 50 mm | |
| 45 mm | 50 mm | |
| 30 mm | 60 mm | |
| Kneading block 6 elements (forward) | 60 mm | 60° |
| Kneading block 6 elements (forward) | 60 mm | 60° |
| 45 mm | 30 mm | |
| 45 mm | 60 mm | |
| Kneading block 6 elements | 60 mm | 90° |
| Kneading disc | 10 mm | |
| Kneading disc | 10 mm | |
| 60 mm | 150 mm | |
| 45 mm | 150 mm | |
| 45 mm | 60 mm | |
| 45 mm | 60 mm | |
| Extruder's discharge | | |

All extruder's elements are double flighted. Kneading element thickness was 2 mm.

Test Methods

As discussed in *Modern Superabsorbent Polymer Technology* (Buchholz, F. L. and Graham, A. T. Eds., Wiley-VCH, New York, 1998, section 4.6.1. *Swelling Capacity: Theory and Practice*, p. 147), several measurement methods can be used to characterize the swelling capacity of a polymer. In the field of superabsorbents, the Gravimetric Swelling Capacity [also called the Free Swell Capacity (FSC)] and the Centrifuge Capacity [also called the Centrifuge Retention Capacity (CRC)] are recommended methods. The FSC and the CRC were used to characterize the swelling capacities of the obtained absorbent products.

Tea bags for FSC and CRC measurements: Tea bags (10× 10 cm) were made from heat sealable Ahlstrom (Chirnside Duns, UK) filter paper (16.5±0.5) g/m$^2$ grade 07291. FSC measurements: The Free Swell Capacity (FSC) in a 0.9% NaCl solution was determined according to the recommended test method WSP 240.2 (05) A from Worldwide Strategic Partners (EDANA-INDA). Tea-bag used was however slightly bigger, as described previously. CRC measurements: The Centrifuge Retention Capacity (CRC) in a 0.9% NaCl solution was determined according to the recommended test method WSP 241.2 (05) A from Worldwide Strategic Partners (EDANA-INDA). The tea-bag used was however slightly bigger, as described previously. AUL measurements: The Absorption Under Load (AUL) at 0.7 Psi, in a 0.9% NaCl solution was determined according to the recommended test method WSP 242.2 (05) A from Worldwide Strategic Partners (EDANA-INDA). Petri dish tray had a bottom surface area of 177 cm$^2$, filter plate had a diameter of 90 mm and piston made from stainless steel. Those factors are not believed to have any significant influences on AUL measurements.

Carboxymethyl Starch Preparation

Wheat starch, having a moisture content of 10.0%, was fed into the extruder with an agitated gravimetric feeder in TSE (ZSE 40 mm), at a throughput of 13.1 kg/hr (28.8 lbs/hr). Sodium chloroacetate, was fed simultaneously with a gravimetric feeder, at a throughput of 5.09 kg/hr (13 lbs/hr). A sodium hydroxide solution (50%) was injected, at a throughput of 4.26 kg/hr (9.4 lbs/hr). Barrels temperatures were B2=29° C., B3=29° C., B4=29° C., B5=43° C., B6=65° C., B7=82° C., B8=82° C., B9=82° C., B10=82° C. Screw speed was set at 200 rpm and screw load at 36-37%. TSE was equipped with a die comprising 10 holes of 3 mm of diameter. Die pressure discharge ranged from 620 kPa to 1.6 MPa (90-232 Psig). An extrudate, having a temperature of 107° C. was conveyed to the pelletizer. The obtained pellets were then pneumatically conveyed to the fluid bed drier where they were dried at 80° C. for about 4 hours. Moisture content ranging from 8 to 11% was obtained. Samples were then ground in a hammer mill to 20-100 Mesh. An average DS of 0.55 was characterized according method ASTM D1439-83a.

Example 1

Surface Treatment of Carboxyalkyl Starches by Acidic Gas Permeation

Figure 3:
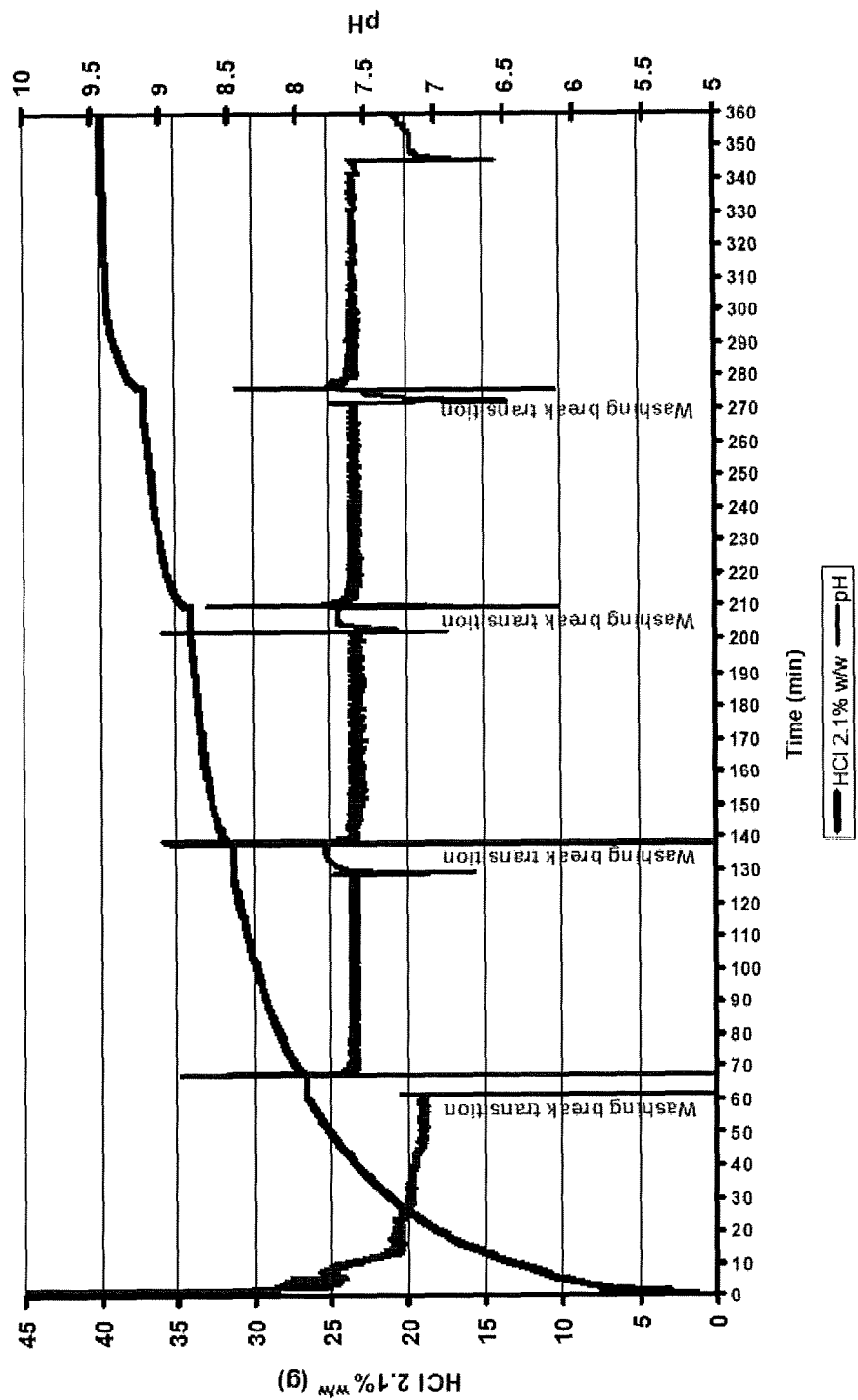
FIG. 3 depicts a pH and HCl addition kinetics graph during carboxylmethyl starch cleaning, according to an embodiment of the present invention.

Ground and dirty CMS (320 Kg; 20-100 Mesh) was added into a 7000 liter double jacketed stainless steel reactor. The reactor was then evacuated to at 20 mm Hg. Nitrogen was injected to equilibrate with ambient pressure (760 mmHg). About 1725 liters of pre-heated solvent (MeOH/H$_2$O, at 82.5% MeOH), at 55-60° C. was injected in the reactor. The slurry was agitated approximately at 100 rpm with a shaft equipped with 68 cm long propellers spaced from 30 cm from the reactor bottom. The mixture pH was adjusted by adding 2.1% (w/w HCl solution The HCl solution was typically prepared using 41.3 ml of HCl, 108.7 ml of tap water and 850 ml of methanol. Hydrochloric acid was added according to a kinetics illustrated in FIG. 3. As the data FIG. 3 was obtained with only 120 g of CMS (dry basis), 2373 times more HCl was used when the reaction was scaled to a larger pilot scale reaction vessel with the same results. Cleaning was divided in 5 sub-washing steps lasting one hour each. At the end of each washing step, carboxymethyl starch particles were allowed to settle and the supernatant liquid was discarded. A particle pH from 6.2 to 6.8 in a 10% suspension was measured at the end of the fifth wash. At the end of the fifth wash, the slurry was pumped with a Wilden pump through 1-1½ pipes to a filter equipped centrifuge. Product was centrifuged for 20 minutes at 400-600 rpm and the pelleted material was transferred into trays, producing a 3-4 cm thick layer of CMA and dried in a stainless steel oven at 60-70° C. for 3-5 days. Agglomerates were obtained and broken in 3 cm pieces and ground to between 20-100 mesh. From this product, 60 g was kept for Example 4.

This procedure was repeated twice. About 906 lbs of those two batches combined was loaded in the dextrinizer. A 180 mm Hg vacuum was made for 5 minutes under a mild mixing. About 1.8 kg (4 lbs) of hydrogen chloride was then added and allowed to react about 30 minutes under a mild mixing. A particle pH ranging from 5.2 to 5.3 was then measured in a % in water suspension of the carboxymethyl starch sample. Then, the carboxymethyl starch was re-vacuumed at 180 mm Hg. Still under mild mixing, the dextrinizer and carboxymethyl starch temperature was raised to 121° C. in about 2 hours. Carboxymethyl starch was treated at 121° C. for 4.5 hours, still under mild agitation. Performances of this product were summarized in Table 2:

TABLE 2

| HCl permeated surface treated CMS | |
|---|---|
| FSC | 31.4 g/g |
| CRC | 19.7 g/g |
| AUL (0.7 psi) | 14.6 g/g |

A sample similar to this one was further analyzed by X-Ray photoelectron spectroscopy. Samples were glued to a cooper disc, allowing them to compensate due to their poor electric conductance. Being a poor conductor, a charge effect was observed at the particles' surface. This was compensated by using a low energy source of electrons (10 eV). Even after this treatment, peaks stayed broad, but were notwithstanding analyzed. Source was monochromatic, with an Al K alpha ray (1486.6 eV) produced by de 10 kV e−, P=150 W. The beams were focused on a spot (1000×750 µm) with LAXL lenses. Sample was ion etched with Ar, 3 kV, with a surface area etched of (1.5 mm×2.5 mm) and with an etching rate of about 25 nm per minute for carbon materials. The pressure was of about $1 \times 10^{-9}$ mbar. The chlorine concentration measured under his Argon abrading technique is depicted in FIG. 5.

Example 2 pH Adjusted and Surface Treated Carboxymethyl Starches by Acidic Gas Permeation

Carboxymethyl starch from the extruder (3980 kg) was loaded in the dextrinizer. The dextrinizer was kept under a 180 mm Hg vacuum with a gentle rotation agitation for 5 minutes. 4.54 kg of gaseous hydrogen chloride was added inside the dextrinizer at a rate of 0.45 kg/min. After adding the gaseous HCl portion, the product was kept under gentle agitation for 5 minutes and a vacuum of 180 mmHg was made. A sample of carboxymethyl starch particles was taken from the dextrinizer to determine its pH in 10% water suspension.

Figure 4:
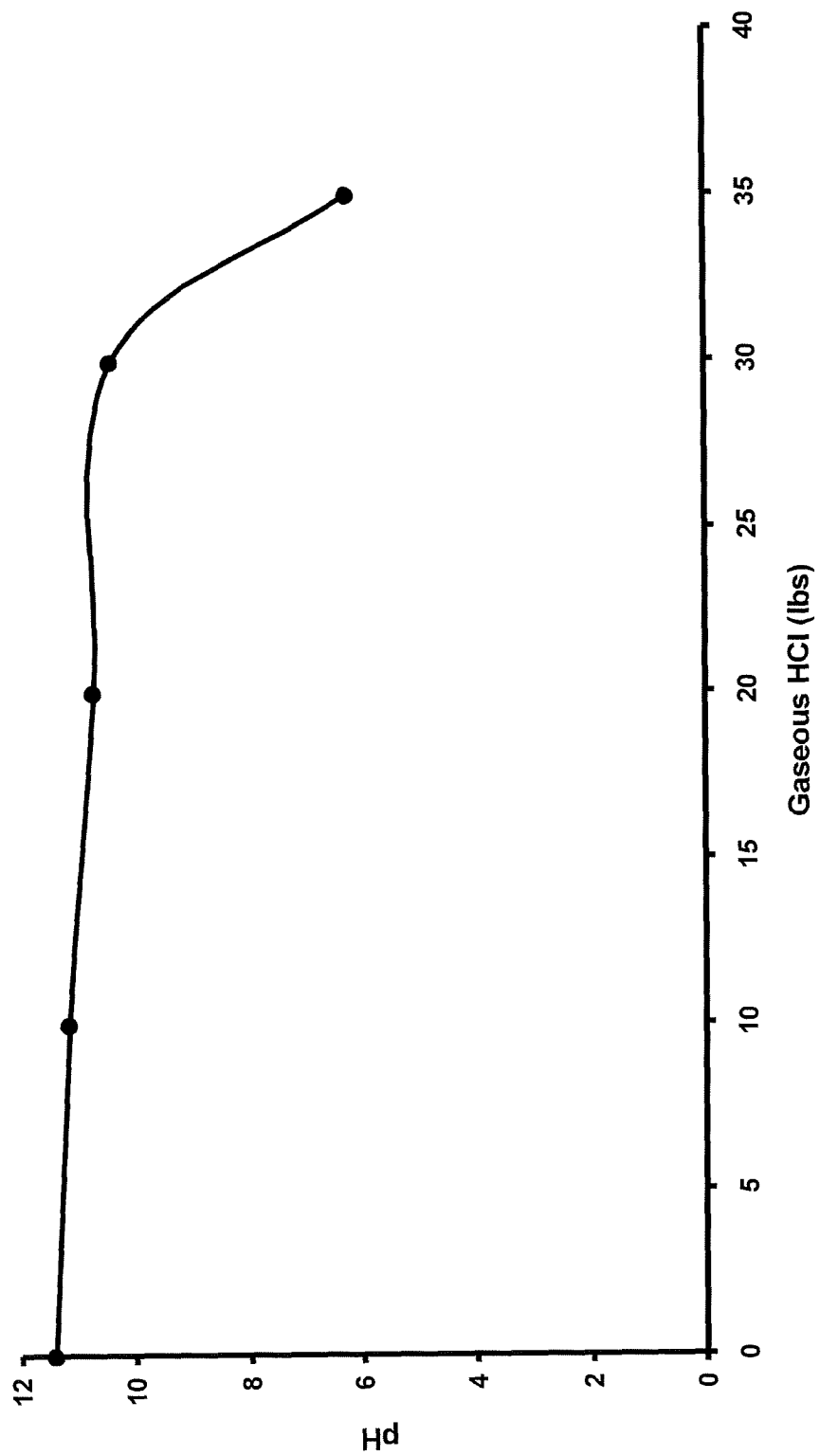
FIG. 4 is graph illustrating a pH adjustment of alkaline carboxymethyl starch extrudates permeated with various amounts of acid gas, according to an embodiment of the present invention.

Another 4.54 kg of gaseous hydrogen chloride was added inside the dextrinizer at a rate of 0.45 kg/min. After adding the gaseous HCl portion, the product was kept under gentle agitation for 5 minutes and the 180 mmHg vacuum was made. A sample of carboxymethyl starch particles was taken from the dextrinizer to determine its pH in 10% water suspension. Another 4.54 kg of gaseous hydrogen chloride was added inside the dextrinizer at a rate of 0.45 kg/min. After adding the gaseous HCl portion, the product was kept under gentle agitation for 5 minutes and the 180 mm Hg vacuum was made. A sample of carboxymethyl starch particles was taken out from the dextrinizer to determine its pH in 10% water suspension. To this stage, a total 13.62 kg of hydrogen chloride was first added and a final 2.27 kg of hydrogen chloride was finally added. The product was subject to a vacuum at 180 mm Hg and discharged from the dextrinizer. Its final pH was 6.27 as measured in a 10% water suspension. All carboxymethyl starch particles samples were measured for their pH. Measurements are shown in FIG. 4.

From the neutralized, but dirty mass of CMS of Example 1, 1.2 kg of CMS was placed in 6000 ml of 85% (v/v) methanol/water solution at 60° C. for 60 minutes. Product was filtered and placed again, for a second time, in 6000 ml of a 85:15 (v/v) methanol/water solution at 60° C. for 60 minutes. Product was filtered and placed again, for a third time, in 6000 ml of a 85:15 (v/v) methanol/water solution at 60° C. for 60 minutes. Product was filtered and placed again, for a fourth time, in 6000 ml of a 85:15 (v/v) methanol/water solution at 60° C. for 60 minutes. Product was filtered and placed again, for a fifth time, in 6000 ml of a 85:15 (v/v) methanol/water solution at 60° C. for 60 minutes. A sample was taken for measurements. A 10% in water suspension having pH of 7.37; a NaCl content of 0.11% and a conductivity of 835 µS/cm was recorded. Resulting solids were then filtered and dried in a convection oven at 65° C. The product formed cakes that were ground to 20-100 mesh.

From the ground mass, 40 g was placed in a 500 ml polypropylene jar which could be closed with a septum equipped lid. A 150 ml polypropylene beaker was placed over the samples and filled with 10 g of NaCl. A syringe comprising 1.5 g of concentrated sulphuric acid was injected over the NaCl beaker, generating hydrogen chloride. This mixture was allowed to react 10 minutes. Thereafter, the pH of the CMS was measured and sulphuric acid was added this way, until the CMS reached a pH of 5.43 in a 10% water suspension. From the resulting CMS, 10 g was placed in a 9 cm crystallizing pan. The CMS was IR heated for 20 minutes at 140° C. Performances of this product are summarized in Table 3:

TABLE 3

| HCl permeated surface treated CMS | |
|---|---|
| FSC | 31.5 g/g |
| CRC | 19.8 g/g |
| AUL (0.7 psi) | 14.8 g/g |

Example 3 pH by Particle Size

From the cleaned and ground mass of Example 2, 60 g was placed in a 500 ml polypropylene jar which could be closed with a septum equipped lid. A 150 ml polypropylene beaker was placed over the samples and filled with 10 g of NaCl. A syringe comprising 0.6 ml of concentrated sulphuric acid was injected over the NaCl beaker, generating hydrogen chloride. CMS particles were sieved on 1180 µm, 850 µm, 600 µm, 425 µm, 300 µm, 250 µm and 150 µm and the pH of these size fractionated particles is shown in FIG. 1.

What is claimed is:

1. An absorbent particle comprising a carboxyalkyl starch that has been permeated with an acidic gas, wherein said particle comprises an inner core region and an outer surface region surrounding the core region, and has a relative amount of intramolecular ester bonds that is evenly dispersed at the surface region and at a greater concentration at the surface region than the inner core region as a consequence of acidic gas-permeation, wherein the intramolecular ester bonds do not comprise a cross linking agent.

2. The absorbent particle of claim 1, wherein the carboxyalkyl starch is carboxymethyl starch.

3. The absorbent particle of claim 1, wherein the acidic gas is hydrogen chloride.

4. The absorbent particle of claim 1, wherein a pH measured in a solution consisting of water and an amount of the surface of the particle is lower than the pH measured in a solution consisting of water and the same amount of the inner core of the particle in a 10% (w/w) suspension of the particles in deionized water.

5. The absorbent particle of claim 1, wherein said absorbent particle exhibits an absorption under load (AUL) at 0.7 psi of at least 14 g/g and a centrifuge retention capacity (CRC) of at least 18 g/g with a solution of 0.7 M NaCl.

6. The absorbent particle of claim 1, wherein said absorbent particle forms discrete gel particles upon swelling with water.

7. The absorbent particle of claim 1, wherein the relative amount of intramolecular ester linkages is indicated with a ferrous chloride/hydroxylamonium test that indicates an amount of ester bonds occurring in the same weight of material taken from the surface of the particle and the inner core region of the particle.

8. The particle of claim 1, wherein said particle comprises an anion obtained from dissociation of the acidic gas.

9. The particle of claim 8 wherein the anion is chlorine.

10. The particle of 9, wherein the relative chlorine concentration is higher at the surface of the particle than in the inner core of the particle when measured by zero second Argon abrading time in comparison to 5400 second Argon abrading time as determined by XPS with the same amount of material taken from the surface and the inner core region of the particle.

11. The particle of claim 10, wherein the chlorine relative concentration is higher than 30% within the first 1500 seconds of Argon abrading time than at 5400 second Argon abrading time as determined by XPS.

12. The particle of claim 1, wherein said particle has: a size ranging from 150 µm to 850 µm; a bulk density from 0.5 g/cm$^3$ to 0.7 g/cm$^3$; and a moisture content no greater than 12%.

13. The particle of claim 1, wherein the carboxyalkyl starch is further characterized by at least one characteristic selected from the group consisting of: a degree of carboxyalkyl substitution ranging from 0.3 to 1.0, an even distribution of carboxyalkyl groups, a pH ranging from 5.5 to 8.0 when measured in a 10% (w/w) suspension of the particles in deionized water, a NaCl content of no greater than 1% (w/w), and a conductivity of no greater than 1500 µS/cm 1 when measured in a 1% (w/w) suspension in water.

14. An absorbent product comprising; the absorbent particle of claim 1 in combination with a co absorbent material.

15. The absorbent product of claim 14 selected from the group consisting of diapers, incontinence articles, feminine hygiene products, printing products, textile products, absorbent paper products, airlaids, absorbent dressings, household articles, sealing materials, humectants, anti-condensation coatings, soil conditioning products, litter products, concrete products, oil-drilling fluids, mining fluids, chemical absorbents, controlled release polymeric gels, detergents, firefighting gels, artificial snow, and food pads.

16. A method for absorbing a liquid comprising contacting the liquid with the absorbent particles of claim 1, wherein the liquid is selected from the group consisting of water, aqueous solutions, physiological fluids and saline solutions.

* * * * *